(12) United States Patent
Hodgson et al.

(10) Patent No.: US 11,504,468 B2
(45) Date of Patent: Nov. 22, 2022

(54) DELIVERY DEVICE

(71) Applicant: ABK Biomedical Incorporated, Halifax (CA)

(72) Inventors: David Mark Douglas Hodgson, Halifax (CA); Marc Andre Gregoire, Stittsville (CA); Kathryn Margaret Ann Atwell, Halifax (CA); Gary Michael Donofrio, Weddington, NC (US); Robert Joseph Abraham, Hammonds Plains (CA); Evan Christopher Wiens, Halifax (CA); Brenna Catherine Kettlewell, Quispamsis (CA)

(73) Assignee: ABK Biomedical Incorporated, Halifax (CA)

( * ) Notice: Subject to any disclaimer, the term of this patent is extended or adjusted under 35 U.S.C. 154(b) by 0 days.

(21) Appl. No.: 17/281,769

(22) PCT Filed: Oct. 18, 2019

(86) PCT No.: PCT/CA2019/051478
§ 371 (c)(1),
(2) Date: Mar. 31, 2021

(87) PCT Pub. No.: WO2020/082168
PCT Pub. Date: Apr. 30, 2020

(65) Prior Publication Data
US 2021/0369947 A1    Dec. 2, 2021

Related U.S. Application Data

(60) Provisional application No. 62/754,355, filed on Nov. 1, 2018, provisional application No. 62/749,322, filed on Oct. 23, 2018.

(51) Int. Cl.
*A61M 5/14* (2006.01)
*A61K 9/00* (2006.01)
(Continued)

(52) U.S. Cl.
CPC ......... *A61M 5/1408* (2013.01); *A61K 9/0019* (2013.01); *A61K 9/16* (2013.01); *A61M 5/16827* (2013.01)

(58) Field of Classification Search
CPC ............ A61M 5/1408; A61M 5/16827; A61K 9/0019; A61K 9/16
See application file for complete search history.

(56) References Cited

U.S. PATENT DOCUMENTS 3,861,386 A * 1/1975 Harris ................. B05B 17/0615
239/338
4,871,360 A    10/1989 Theeuwes
(Continued)

FOREIGN PATENT DOCUMENTS

CN         103648466 A      3/2014
WO       2018/107126 A1     6/2018

OTHER PUBLICATIONS

International Application No. PCT/CA2019/051478, International Search Report and Written Opinion dated Dec. 19, 2019.
(Continued)

*Primary Examiner* — Lauren P Farrar
(74) *Attorney, Agent, or Firm* — Borden Ladner Gervais LLP; David Nauman

(57) ABSTRACT

A delivery device for intravenous delivery of microparticles to a patient. The delivery device is fluidly connectable to (i) a first source of an injection medium and (ii) a second source of an injection medium. The delivery device includes: a first fluid inlet fluidly connectable to the first source of the injection medium, a fluid outlet, a fluid mixer fluidly con-
(Continued)

necting the first fluid inlet to the fluid outlet, a second fluid inlet fluidly connectable to the second source of the injection medium, and a source of microparticles fluidly connecting the second fluid inlet to the fluid mixer. When fluid flows from the second source of the injection medium into the delivery device: the second injection medium fluidly drives microparticles from the source of microparticles into the fluid mixer, and the fluid outlet dispenses to the patient an injection medium that includes the microparticles.

25 Claims, 9 Drawing Sheets

(51) Int. Cl.
*A61K 9/16* (2006.01)
*A61M 5/168* (2006.01)

(56) References Cited

U.S. PATENT DOCUMENTS

| | | | | |
|---|---|---|---|---|
| 4,908,019 | A | 3/1990 | Urquhart et al. | |
| 5,902,273 | A | 5/1999 | Yang et al. | |
| 6,331,317 | B1 | 12/2001 | Lyons et al. | |
| 6,387,077 | B1 | 5/2002 | Klibanov et al. | |
| 6,575,930 | B1 | 6/2003 | Trombley et al. | |
| 2009/0005734 | A1* | 1/2009 | Herbette ........... | A61M 5/16827 604/113 |
| 2009/0247985 | A1 | 10/2009 | Melsheimer et al. | |
| 2011/0245799 | A1 | 10/2011 | Erickson et al. | |
| 2016/0228129 | A1 | 8/2016 | Levy | |
| 2017/0151357 | A1* | 6/2017 | Cade .................. | A61K 51/1244 |
| 2017/0304151 | A1 | 10/2017 | Van Den Berg et al. | |

OTHER PUBLICATIONS

European Patent Application No. 19876598.4, Extended European Search Report dated Jul. 6, 2022.
Chinese Patent Application No. 2019800688489, Office Action dated Sep. 1, 2022 and English Translation.

* cited by examiner

DELIVERY DEVICE

CROSS-REFERENCE TO RELATED APPLICATIONS

This application claims the benefit of priority of U.S. Provisional Patent Application No. 62/749,322 filed Oct. 23, 2018; and of U.S. Provisional Patent Application No. 62/754,355 filed Nov. 1, 2018, which are hereby incorporated by reference.

FIELD

The present disclosure relates to a device for delivering microparticles to a patient.

BACKGROUND

The following paragraphs are not an admission that anything discussed in them is prior art or part of the knowledge of persons skilled in the art.

Microparticles are employed by interventional radiologists for the selective occlusion of blood vessels in the treatment of, for example, hypervascular tumors such as leiomyoma uteri, and vascular anomalies such as vascular malformations. Such microparticles are injected into a hepatic artery of a patient.

Selective internal radiation therapy (SIRT) may be used to treat primary or metastatic hepatic malignancies. In SIRT, yttrium-90 ($^{90}Y$) radiolabeled microparticles are injected into a hepatic artery of a patient, preferentially localizing in the hepatic tumours due to their increased vascularization. The radioactive yttrium-90 labeled microparticles decay and deliver radiation to the surrounding tissue.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Microparticles are injected intravenously into a patient with an injection medium, such as an aqueous intravenous solution. However, when the microparticles have a substantially higher density than the injection medium (such as glass microparticles in an aqueous solution) the microparticles may settle together making it difficult to inject the microparticles into the patient. It may be especially difficult to administer the microparticles at a slow and consistent rate.

BTG attempts to address this problem with their TheraSphere™ yttrium-90 glass microspheres product by flowing the injection medium up through the bottom of the settled microparticles to generate in the delivery device a fluidized bed of microparticles in a constant volume reservoir. Fluidized microparticles are carried along with the injection medium to the patient. This approach may require an undesirably high flow rate of injection medium to fluidize microparticles that are significantly more dense than the injection medium (such as glass microparticles in a saline solution). This approach may result in an injection medium with inconsistent concentrations of microparticles delivered over time, irrespective of the density of the microparticles. That is, fluidizing microparticles may result in administration of inconsistent concentrations for microparticles that are significantly more dense than the injection medium, and for microparticles are close in density to the injection medium (such as resin-based microparticles in a saline solution).

Therefore, there remains a need for a delivery device that, in operation, can be used to intravenously administer microparticles to a patient, such as at a slow and/or consistent rate.

In one aspect, the present disclosure provides a delivery device that includes a first fluid inlet, a second fluid inlet, a fluid mixer, a source of microparticles, and a fluid outlet. The fluid mixer is fluidly connected to the source of microparticles and is fluidly connectable to a first source of an injection medium through the first fluid inlet. The source of microparticles is fluidly connectable to a second source of an injection medium through the second fluid inlet. The fluid mixer is fluidly connected to the fluid outlet for delivery of the injection medium.

In another aspect, the present disclosure provides a method of delivering microparticles to a patient. The method includes: flowing a first injection medium into a first arm of a fluid mixer and out a second arm of the fluid mixer, and flowing a second injection medium into the third arm of the fluid mixer, where the second injection medium fluidly drives microparticles that are loaded in an elongate housing into the first injection medium; and intravenously administering to the patient the resulting mixture of the microparticles, the first injection medium, and the second injection medium. The flow of the first injection medium is independent of the flow of the second injection medium.

BRIEF DESCRIPTION OF THE DRAWINGS

Embodiments of the present disclosure will now be described, by way of example only, with reference to the attached Figures.

DETAILED DESCRIPTION

Figure 1:
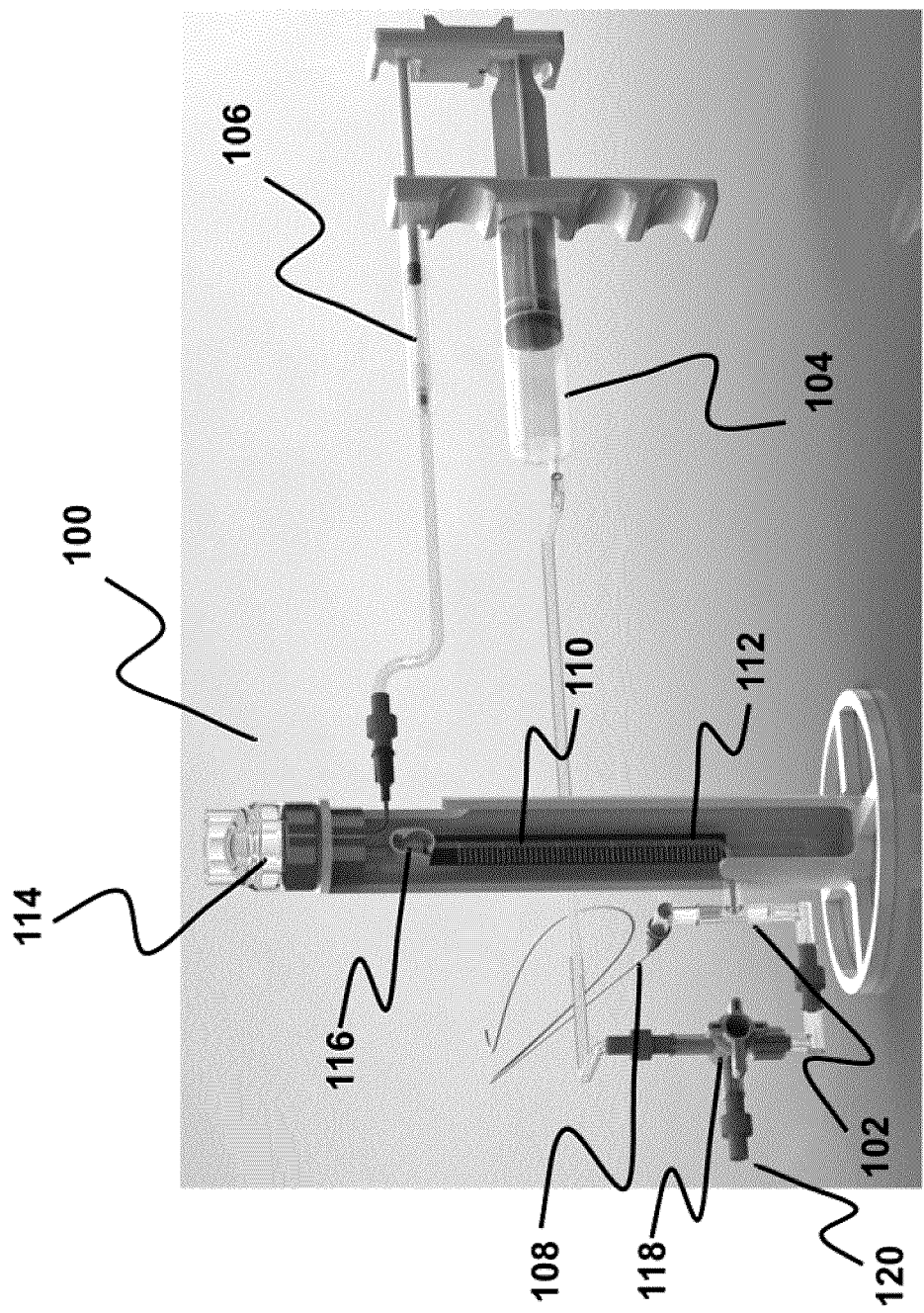
FIG. 1 is an illustration of an exemplary delivery device according to the present disclosure.

Generally, the present disclosure provides a delivery device that includes a first fluid inlet, a second fluid inlet, a fluid mixer, a source of microparticles, and a fluid outlet. The fluid mixer is fluidly connected to the source of microparticles and is fluidly connectable to a first source of an injection medium, referred to as the transport medium, through the first fluid inlet. The source of microparticles is fluidly connectable to a second source of an injection medium, referred to as a displacement medium, through the second fluid inlet. The fluid mixer is fluidly connected to the fluid outlet for delivery of the transport medium and the displacement medium, such as to a patient via an intravenous catheter.

During operation, fluid driven from the source of the displacement medium into the delivery device fluidly drives microparticles from the source of microparticles into the fluid mixer.

The first and second fluid inlets allow the flow of the transport medium, and the displacement medium through the fluid mixer to be independent of each other.

In the context of the present disclosure, a "fluid mixer" should be understood to refer to any combination of components that mixes the transport medium with the displacement medium when both the transport medium and the displacement medium are flowing to the fluid outlet. The displacement medium carries in it at least some microparticles when the source of microparticles is loaded with microparticles.

For example, the fluid mixer may be a T-junction, such as a chromatographic T-junction, or a Y-junction. In one example, the fluid mixer may include a conduit for the transport medium, where the conduit fluidly connects the source of the transport medium to the fluid outlet. The fluid mixer may also include a dispenser disposed within the conduit for adding microparticles to the transport medium passing through the fluid mixer. The dispenser directs the microparticles in the direction of the flow of the transport medium. In a specific example, the fluid mixer may include two concentric tubes, with (a) the outer tube conveying the transport medium from the source of the transport medium, to the fluid outlet and (b) the inner tube conveying microparticles from the source of microparticles into the transport medium in the direction of the flow of the transport medium.

The source of microparticles may include an elongate housing, such as tubing, holding or containing the microparticles. The elongate housing holding the microparticles is fluidly connected at one end to the fluid mixer and fluidly connectable at a distal end to the source of the displacement medium. During operation, fluid driven from the source of the displacement medium into the distal end of the elongate housing fluidly drives microparticles located in the elongate housing from the elongate housing and into the fluid mixer.

In some examples, the dispenser in the fluid mixer may have a portion that is positioned substantially horizontally when the delivery device is in the delivery orientation. In other examples, the dispenser in the fluid mixer may have a portion that is positioned substantially vertically when the delivery device is in the delivery orientation.

In exemplary dispensers, the cross sectional area of the flow path for the microparticles is sufficiently large and sufficiently constant that the fluid flow is not materially restricted at a given operational flow rate and with the microparticles being delivered. For example, the diameter of the flow path for the microparticles may be at least three times the average diameter of the microparticles being administered; and/or the elongate housing containing the microparticles may have the same cross sectional area as the opening in the fluid mixer for injection of the microparticles. It should be understood that the cross sectional area is "sufficiently constant" for a given flow rate, and that the cross sectional area of the flow path for the microparticles may be smaller before the fluid mixer and larger after the fluid mixer in order to account for the increase in flow rate of the combination of the transport medium and the displacement medium compared to the flow rate of the displacement medium.

In exemplary dispensers where the fluid mixer includes a microparticle dispenser disposed within a conduit, the cross section of the conduit may be sufficiently large in comparison to the cross section of the dispenser that the dispenser does not materially restrict the fluid flow through the fluid mixer (at operational flow rates).

During operation, the delivery device is fluidly connected to the transport medium and the displacement medium. The transport medium flows from the source of the transport medium, through the fluid mixer and is delivered through the fluid outlet. The transport medium may be intravenously administered to the patient, such as via a catheter. In the absence of any flow from the source of displacement medium, the fluid mixer delivers the transport medium with substantially no microparticles. However, when the source of displacement medium flows into the delivery device, the microparticles are fluidly driven from the source of microparticles into the transport medium passing through the fluid mixer and are carried by the mixture of transport medium and displacement medium through the fluid outlet for delivery to the patient.

For a given flow rate of the transport medium, the delivery rate of the microparticles to the patient is at least partially determined by the flow rate of the displacement medium. A higher flow rate pushes more microparticles into the fluid mixer per unit time, and results in a higher rate of administration of the microparticles. A lower flow rate pushes fewer microparticles into the fluid mixer per unit time, and results in a lower rate of administration of the microparticles.

Although the flow rates of the first and second injection mediums may be selected together and coupled to provide a desired delivery rate of the microparticles, the flow of the transport medium is independent of the flow of the displacement medium.

The flow rate of the transport medium may be from 2 to 80 times, such as from 10 to 50 times or from 20 to 40 times, the flow rate of the displacement medium. The flow rate of the combination of the transport and displacement mediums may be a flow rate that is substantially the same as the flow rate of the blood stream in the patient, such as a flow rate up to about 0.5 mL/s. The microparticles may be, in the elongate housing, at a packing efficiency from about 80% to about 40%. Packing efficiency refers to the volume of microsphere relative to the total volume of the elongate housing. The delivery device may provide from about 1 mg to about 200 mg of microparticles per total mL of injection medium, i.e., the combined volume of the first and second injection mediums. The microparticles may have a specific gravity that is greater than a specific gravity of the transport medium. In an example, the microparticles may have a specific gravity from about 3.3 to about 3.9 with reference to water.

The delivery device may also define a chamber that is fluidly connected to the elongate housing and located fluidly between the elongate housing and the displacement medium. The chamber is sized to hold at least all of the microparticles in the delivery device, and may be used to load microparticles into the elongate housing.

The chamber may include a conical portion that funnels microparticles from the chamber into the elongate housing when the delivery device is in a loading orientation, such as an orientation where the chamber is located substantially above the elongate housing. When the delivery device is in a fluid filling orientation, such as an orientation where the elongate housing is positioned substantially above the chamber, the microparticles remain in the chamber.

To load the elongate housing with microparticles, the delivery device may be positioned in the fluid filling orientation to allow substantially all of the microparticles to fall into the chamber located substantially below the elongate housing. If the elongate housing is not filled with loading fluid, the delivery device may be connected to a fluid source, such as displacement medium, and the elongate housing may be filled from the bottom end that is fluidly connected to the chamber to the top end that is fluidly connected to the fluid mixer. Once the elongate housing is filled with the loading fluid, the delivery device may be positioned in the loading orientation. Microparticles located in the chamber are funneled into the elongate housing, which may be located substantially below the chamber. Microparticles that are more dense than the loading fluid settle into and pack the elongate housing faster than microparticles that are close in density to the loading fluid.

In the context of the present disclosure, "substantially above" and "substantially below" should be understood in the context of how fluids flow. Microparticles may fall from the elongate housing into the chamber if, for example, the elongate housing is titled at a 45 degree angle and the chamber is not directly below the elongate housing. Microparticles may fall from the chamber into the elongate housing if, for example, the chamber is not directly above the elongate housing, but the funnel is sufficiently angled to direct the microparticles into the elongate housing.

When the source of microparticles includes an elongate housing, the delivery device may include a microparticle trap fluidly connecting the fluid mixer to the elongate housing. In the loading orientation, the microparticles are funneled into the elongate housing and are stopped from entering the fluid mixer by the microparticle trap. The trap may be, for example, an approximately 90 degree bend or a U-turn in tubing connecting the elongate housing to the fluid mixer.

The delivery device may alternatively define a chamber that is fluidly connected to the elongate housing, but not located fluidly between the elongate housing and the displacement medium. The chamber is sized to hold at least all of the microparticles that are to be loaded into the elongate housing. The chamber may be fluidly located outside of the fluid flow path from the displacement medium to the liquid outlet. To load the elongate housing with the microparticles, the microparticles in the chamber may be transported from the chamber, optionally through the fluid mixer, and into the elongate housing. The microparticles may be transported by flowing a loading fluid from the chamber through the elongate housing and out of a loading fluid outlet. A filter may be located between the elongate housing and the loading fluid outlet to prevent or inhibit microparticles from being transported out of the delivery device.

The loading fluid and microparticles may be drawn from the chamber by applying a reduced pressure at the loading fluid outlet, such as using an aspirating syringe. Alternatively, the loading fluid and microparticles may be drawn from the chamber by applying a reduced pressure at the source of the displacement fluid.

The loading fluid and microparticles may be forced from the chamber by applying a positive pressured to the chamber, such as by injecting a gas or loading fluid into the chamber and displacing the microparticles into the elongate housing.

The present disclosure also generally provides a device that can be loaded with microparticles. Such a device includes a first fluid inlet, a second fluid inlet, a fluid mixer, a receptacle configured to hold microparticles, and a fluid outlet. The fluid mixer is fluidly connected to the receptacle and is fluidly connectable to a first source of an injection medium, referred to as the transport medium, through the first fluid inlet. The receptacle is fluidly connectable to a second source of an injection medium, referred to as a displacement medium, through the second fluid inlet. The fluid mixer is fluidly connected to the fluid outlet.

When the receptacle holds microparticles, the device is referred to as a delivery device and the receptacle is referred to as a source of microparticles for the delivery device. As described above, the receptacle may include an elongate housing, such as tubing, configured to hold or contain the microparticles. The receptacle, for example the elongate housing, may be fluidly connectable to the source of displacement medium at a first end and fluidly connected to the fluid mixer at a second end.

The device may additionally include a loading fluid inlet fluidly coupled to the receptacle. A supply of microparticles may be fluidly connectable to the receptacle through the loading fluid inlet. The supply of microparticles may be provided in a chamber. The supply of microparticles may be provided separately from the device. The device may include a loading fluid outlet, where the receptacle is fluidly located between the loading inlet and the loading fluid outlet. For example, the first end of the receptacle may be fluidly connected to the loading fluid outlet, and the second end of the receptacle may be fluidly connected to the loading fluid inlet through the fluid mixer. In another example, the first end of the receptacle may be fluidly connected to the loading fluid inlet, and the second end of the receptacle may be fluidly connected to the loading fluid outlet, which may be the same as the fluid outlet.

The device may include a filter fluidly located between the receptacle and the loading fluid outlet. The filter may prevent or inhibit microparticles from flowing out of the loading fluid outlet when the receptacle is being loaded with microparticles from the supply of microparticles.

The delivery device may additionally include a source of flushing medium fluidly connectable to a fluid outlet via the elongate housing. The flushing medium may be used to flush microparticles from the elongate housing, for example if not all of the microparticles are administered to a patient. The flushing medium may be used to prime the delivery device with a liquid.

The present disclosure also generally provides a method of delivering microparticles to a patient. The method includes: flowing a first injection medium, referred to as the transport medium, into a first arm of a fluid mixer and out a second arm of the fluid mixer, and flowing a second injection medium, referred to as the displacement medium, into the third arm of the fluid mixer, where the displacement medium fluidly drives microparticles that are loaded in an elongate housing into the transport medium; and intravenously administering to the patient the resulting mixture of the microparticles, the transport medium, and the displacement medium. The flow of the transport medium is independent of the flow of displacement medium.

The relative flow rate of the transport medium versus the flow rate of the displacement medium determines the concentration of microparticles (such as in mg per mL) delivered to the patient. The absolute flow rates (such as in mL per second) of the transport medium and the displacement medium determines the delivery rate of microparticles to the patient. The method may administer to the patient about 1 mg of microparticles per second to about 200 mg of microparticles per second. In some examples, the method may administer to the patient about 1 mg of microparticles per second to about 60 mg of microparticles per second; or about 1 mg of microparticles per second to about 30 mg of microparticles per second. In particular examples, the method may administer to the patient about 10 mg of microparticles per second to about 20 mg of microparticles per second.

It should be understood that the authors of the present disclosure contemplate combining any and all of the exemplary subject matter discussed above, unless the subject matter refers to alternatives.

One example of a delivery device according to the present disclosure is illustrated in FIG. 1. The delivery device (100) is illustrated with a fluid mixer (102) being fluidly connected to a first source of injection medium, referred to as a source of transport medium (104), and a second source of injection medium, referred to as a source of displacement medium (106), and fluidly connected to a fluid outlet (108). It should be understood that the delivery device may be manufactured, sold, or delivered without these fluid connections in place.

The delivery device (100) is illustrated with tubing forming an elongate housing (110). The elongate housing (110) includes, in the illustrated orientation, a vertical portion (112). The elongate housing (110) is fluidly connected to the fluid mixer (102) at one end, and fluidly connected to the source of displacement medium (106) at the opposite end.

The delivery device (100) defines a chamber (114) fluidly located between the elongate housing (110) and the source of displacement medium (106). An optional clip (116) is illustrated between the chamber (114) and the elongate housing (110). The clip (116) may be used to stop or reduce flow of fluid and/or microparticles between the chamber (114) and the elongate housing (110).

In operation, transport medium from the source of transport medium (104), travels through the fluid mixer (102) and out the fluid outlet (108). The displacement medium delivered from the source (106) of displacement medium, travels through the chamber (114), into the elongate housing (110), and pushes microparticles located in the elongate housing (110) into the fluid mixer (102). The transport medium travelling through the fluid mixer (102) carries the microparticles out the fluid outlet (108) for delivery of the transport medium, including the microparticles and the displacement medium, to the patient. The fluid outlet (108) is illustrated as tubing. During delivery, the tubing may be fluidly connected to the patient using any suitable mechanism. For example, the tubing may be fluidly connected to a peripheral venous catheter that is inserted into the patient.

The ratio of fluid delivery of the source of transport medium and the source of displacement medium at least partially determines the delivery rate of the microparticles to the patient. In the illustrated delivery device (100), the source of transport medium (104) and the source of displacement medium (106) are shown as syringes that are coupled together, with the two plungers in the two syringes experiencing the same linear displacement. Coupling the two syringes together in this manner allows the ratio of fluid delivery to be set by the ratio of cross sectional areas of the two syringes. The first syringe may be a 20 mL syringe and the second syringe may be a 0.5 mL syringe, with the two syringes having the same linear displacement for injection. Coupling such syringes together provides a 40:1 v/v ratio of fluid delivery for the transport medium to the displacement medium.

Although the source of the transport medium (104) and the source of the displacement medium (106) are illustrated in FIG. 1 as syringes, the sources may be any fluid injection devices, and may be the same or different. This also applies to the devices illustrated in the other figures. For example: the source of the transport medium may be an IV bag connected to a peristaltic pump, and the source of displacement medium may be a syringe. Alternatively, or both the source of the transport medium and the source of the displacement medium may be syringes. The source of the transport medium and the source of the displacement medium may be the same source of medium, but separately connected and independently flowable to the delivery device. For example, the delivery device may be fluidly connected to a single IV bag through two different sets of tubing. The first set of tubing may be connected to a peristaltic pump that pumps fluid into the fluid mixer, and the second set of tubing may be connected to a peristaltic pump that pumps fluid into the source of microparticles.

The transport medium and the displacement medium may be the same or may be different. For example: the transport medium may be saline, while the displacement medium may be deionized water; or both the transport and the displacement mediums may be saline.

The delivery device (100) is also illustrated with an optional T-port valve (118). The T-port valve (118) allows fluid, such as transport medium, to be drawn from an inlet (120) into only the first injector, into only the second injector, or into both injectors at the same time.

Figure 2:
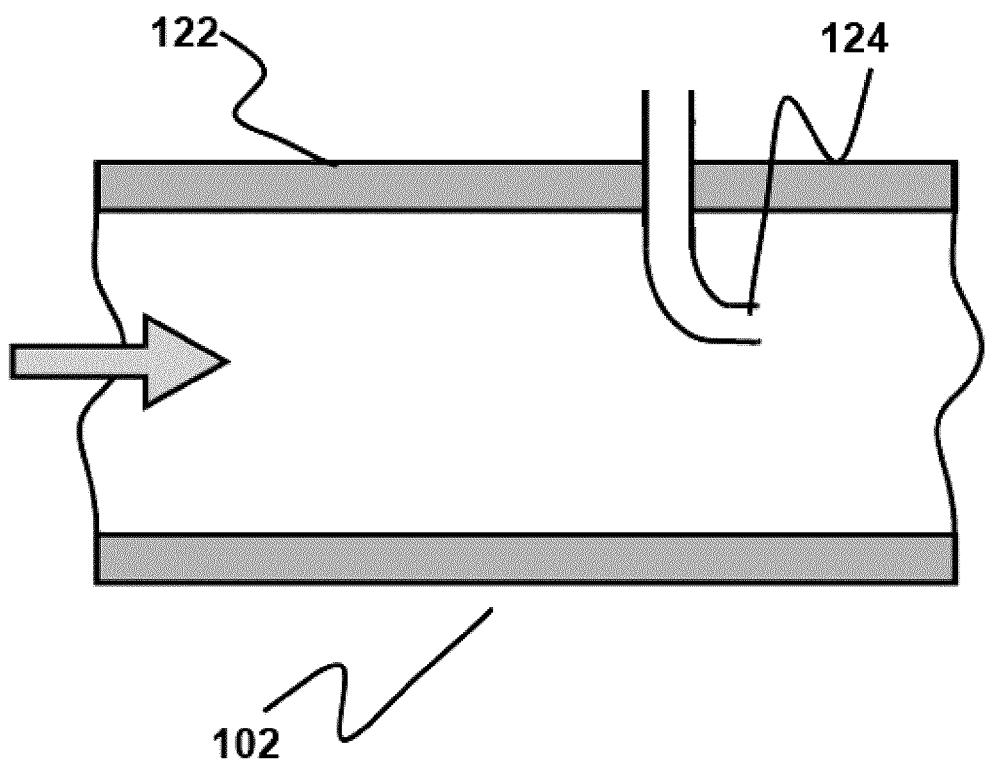
FIG. 2 is a cross-section illustration of an exemplary fluid mixer which may be used in a delivery device according to the present disclosure.

The fluid mixer (102) is generally illustrated in FIG. 2, where the arrow indicates the direction of flow of the transport medium from the source of the transport medium (not shown) to the fluid outlet (not shown). The fluid mixer includes a conduit (122) and a dispenser (124) disposed within the conduit. The dispenser (124) adds microparticles to the transport medium passing through the fluid mixer, and directs the microparticles in the direction of the flow of the transport medium. The dispenser may be substantially concentric with the conduit, directing the microparticles into the center of the fluid flow.

Figure 3:
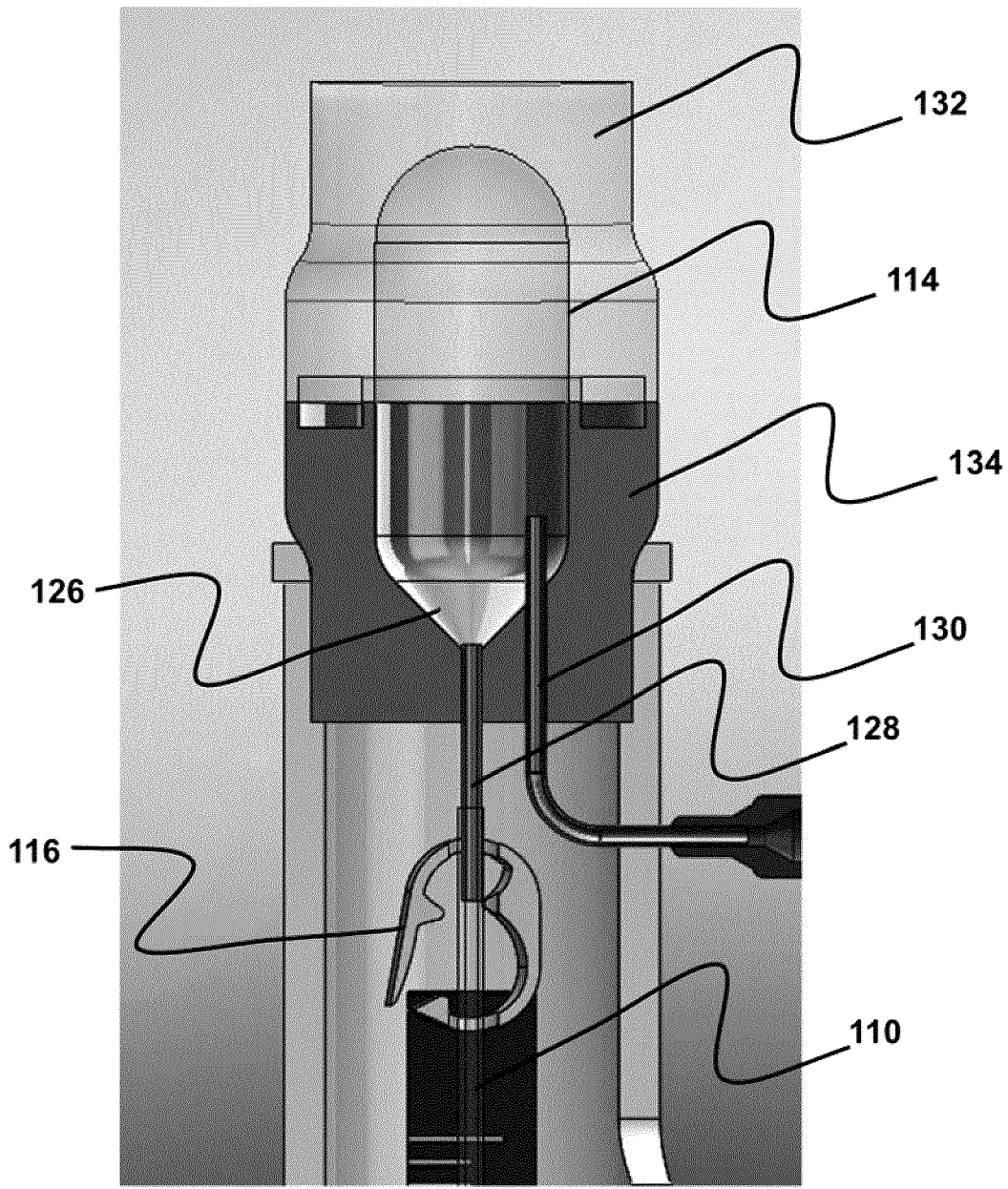
FIG. 3 is a cross-sectional illustration of a portion of the exemplary delivery device, positioned in the loading orientation.

The chamber (114) is illustrated in cross section in FIG. 3. The chamber (114) includes a conical portion (126). In the illustrated orientation, the conical portion (126) is located at the bottom of the chamber, and funnels microparticles into the elongate housing (110). FIG. 3 also illustrates that the elongate housing (110), the chamber (114), and the source of the displacement medium (not shown) are at least fluidly connected through metal fittings (128 and 130). The chamber (114) is also illustrated as being formed from the connection of two separate pieces of housing (132 and 134). During manufacture of the delivery device, the microparticles may be added to one of the two pieces of housing and the two pieces of housing may be joined together to form the chamber (114). The optional clip (116) may be closed to reduce or prevent microparticles from escaping the chamber (114), such as during transportation.

Figure 4:
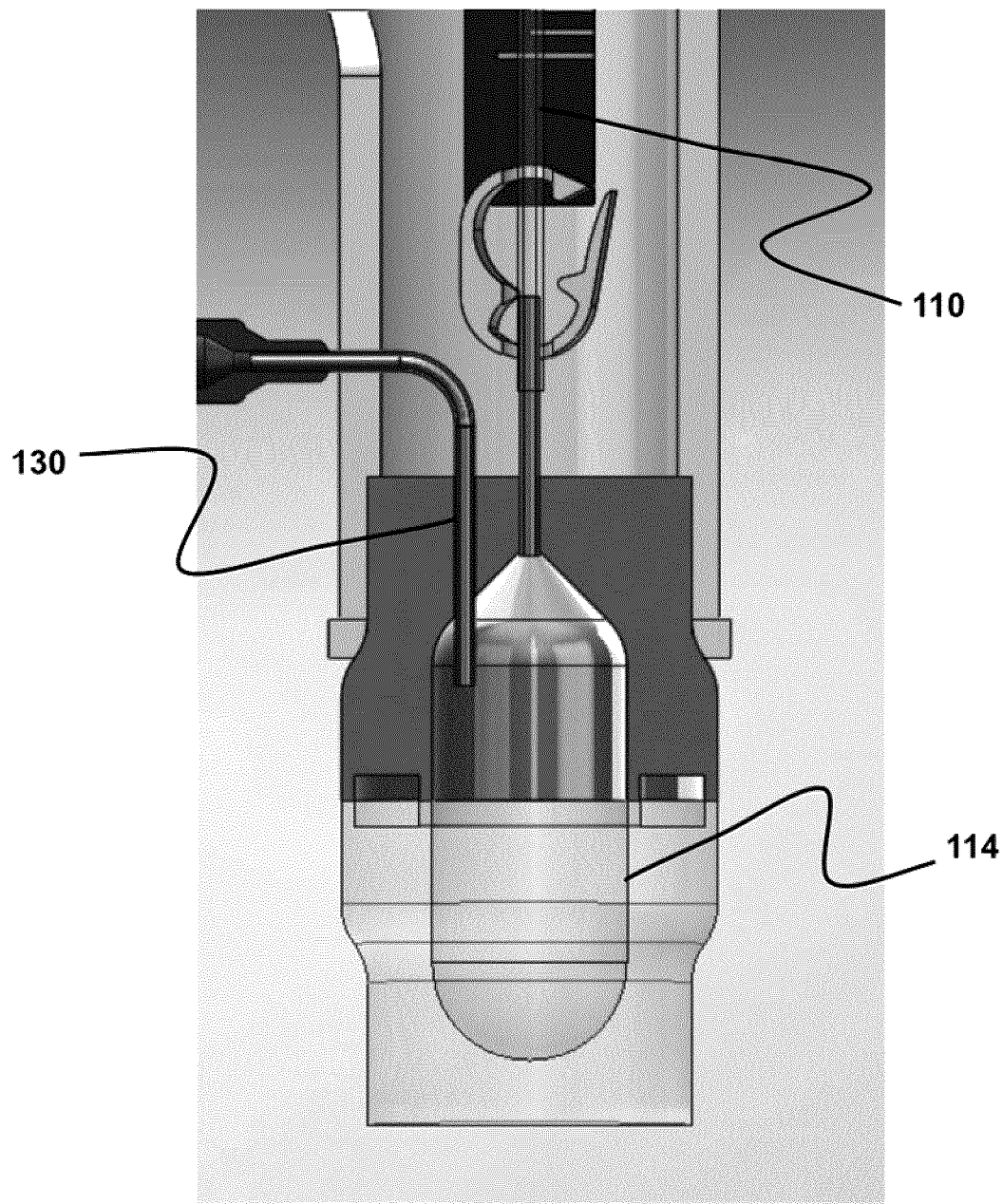
FIG. 4 is a cross-sectional illustration of a portion of the exemplary delivery device, positioned in the fluid-filling orientation.

The delivery device (100) and the chamber (114) are illustrated in the loading orientation in FIGS. 1 and 3. The chamber (114) is illustrated in the fluid-filling orientation in FIG. 4. In the fluid-filling orientation, the elongate housing (110) is located above the chamber (114), and the microparticles are collected into the chamber (114). The displacement medium may be added to the chamber (114) through the fitting (130) that fluidly connects the chamber (114) to the source of the displacement medium. The added displacement medium, once it fills the chamber (114), may then fill the elongate housing (110). Adding the displacement medium at a flow rate that avoids fluidizing the microparticles allows the elongate housing (110) to be filled without carrying a significant number of microparticles into the elongate housing (110).

Once the chamber (114) and elongate housing (110) are filled with fluid, the delivery device may be returned to the loading orientation illustration in FIG. 1. Microparticles located in the chamber (114) are then funneled into the elongate housing (110) by the conical portion (126) of the chamber (114).

Figure 5:
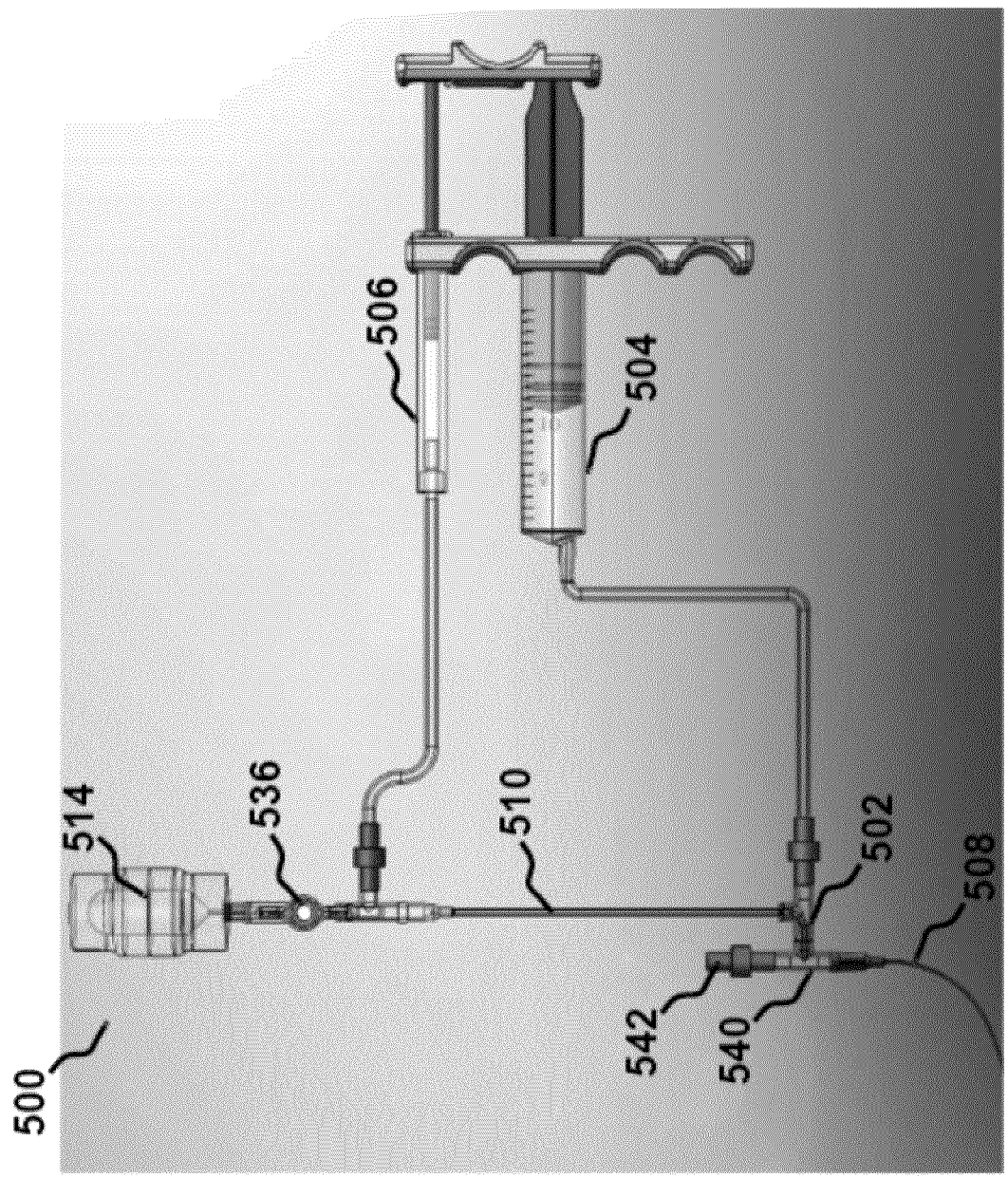
FIG. 5 is a side view of another example of a delivery device according to the present disclosure.
Figure 8:
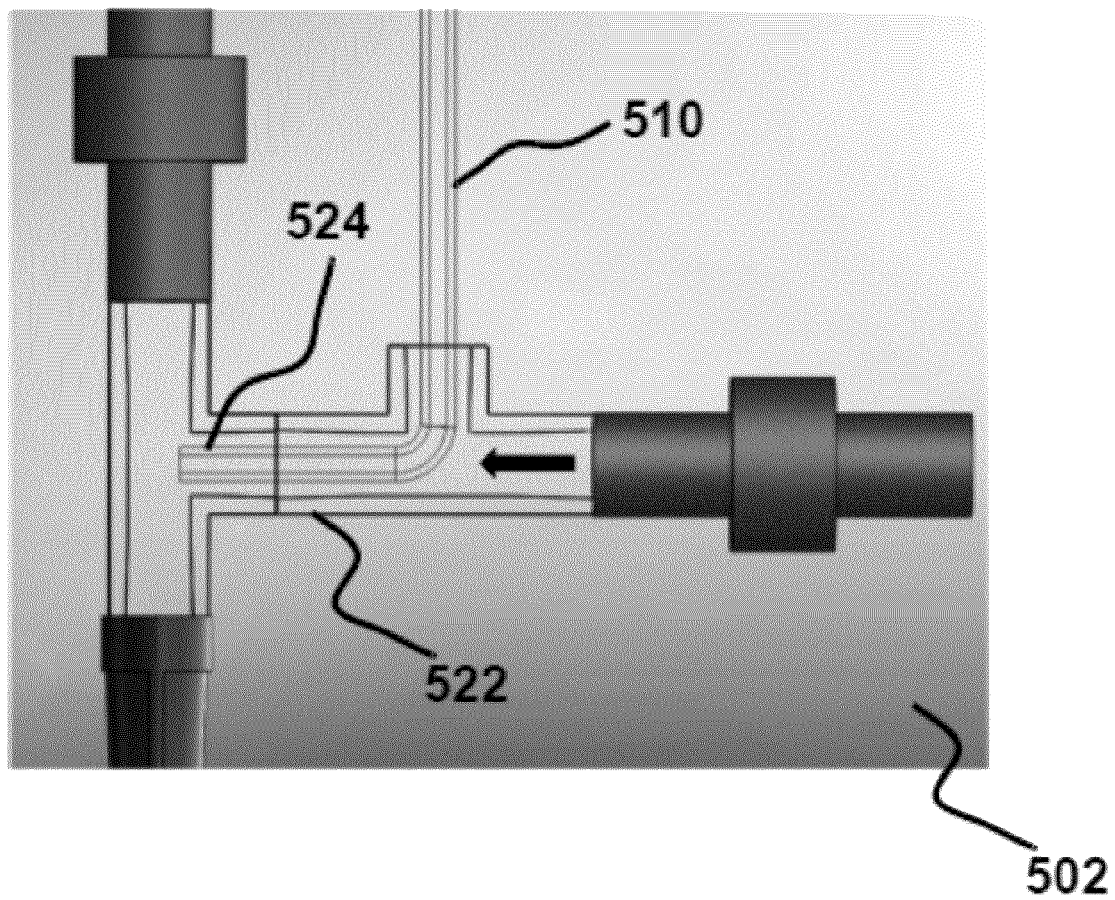
FIG. 8 is a side view of an example of a fluid mixer of the delivery device of FIG. 4.

Reference is now made to FIG. 5, which through FIG. 8, which illustrate another example of a delivery device in accordance with the present disclosure. Many of the features of the delivery device illustrated in FIG. 5 are similar to those shown and described above with reference to FIG. 1 through FIG. 4 and are not described again in detail to avoid obscuring the description. Where similar features are described with reference to FIG. 5, similar reference numerals are utilized, raised by 400.

The delivery device (500) in FIG. 5 is illustrated with a fluid mixer (502) fluidly coupled to a source of transport medium (504), and a source of displacement medium (506), and fluidly coupled to a fluid outlet (508).

The delivery device (500) includes the elongate housing (510), which in the present example is tubing. The elongate housing (510) is fluidly coupled to the fluid mixer (502) at a second end, and fluidly coupled to the source of displacement medium (506) at a first end.

In the example illustrated in FIG. 5, the fluid mixer (502) is coupled to the fluid outlet (508) by a T-junction (540). The T-junction (540) includes a check valve (542) that is coupleable to a flushing fluid to facilitate flushing of microparticles out of the outlet (508).

The chamber (514) in the present example, is also fluidly coupled to the first end of elongate housing (510), via a fluid control valve (536) for controlling the flow of microparticles into the elongate housing (510). Thus, in the present example, the source of the displacement medium (506) is coupled directly to the elongate housing (510), rather than directly to the chamber, as in the first example described above with reference to FIG. 1.

In operation, transport medium from the source of transport medium (504), travels through the fluid mixer (502) and out the fluid outlet (508).

The fluid control valve (536) may be opened to facilitate the flow of the microparticles and fluid from the chamber (514) into the elongate housing (510). The displacement medium delivered from the source (506) of displacement medium, travels into the elongate housing (510), and pushes microparticles from the elongate housing (510) into the fluid mixer (502). The transport medium travelling through the fluid mixer (502) carries the microparticles out the fluid outlet (508) for delivery of the transport medium, including the microparticles and the displacement medium, to the patient.

Figure 6:
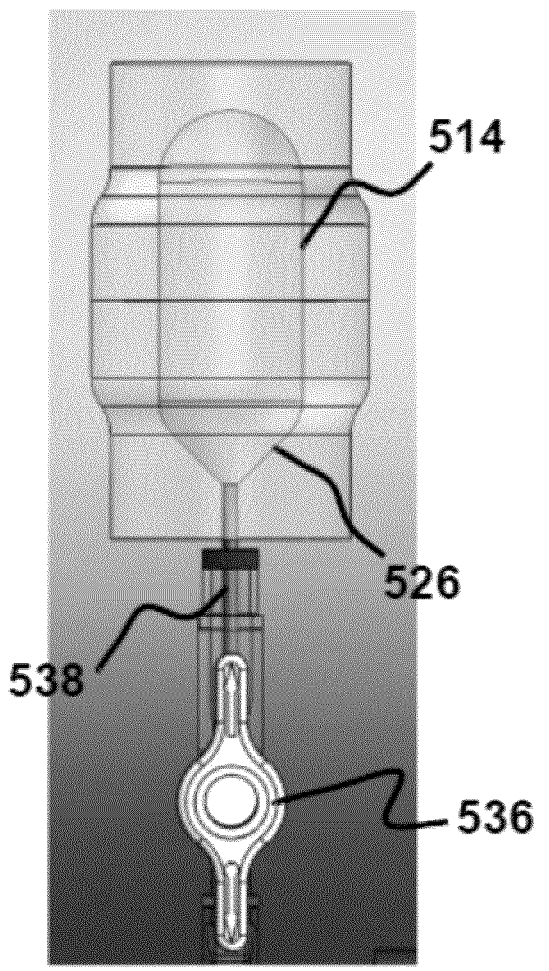
FIG. 6 is side view of a portion of the delivery device of FIG. 5, with parts illustrated as transparent to show interior detail.

The chamber (514) and the fluid control valve (536) are illustrated in FIG. 6. The chamber (514) includes a conical portion (526) for funneling microparticles, and a carrier fluid disposed in the chamber (514), through tubing 538, and into the elongate housing (510) when the fluid control valve (536) is in an opened position. The fluid control valve (536) is closable to reduce or inhibit the flow the flow of microparticles into the elongate housing (510). The tubing 538 fluidly couples the chamber (514) with the fluid control valve (536).

Figure 7:
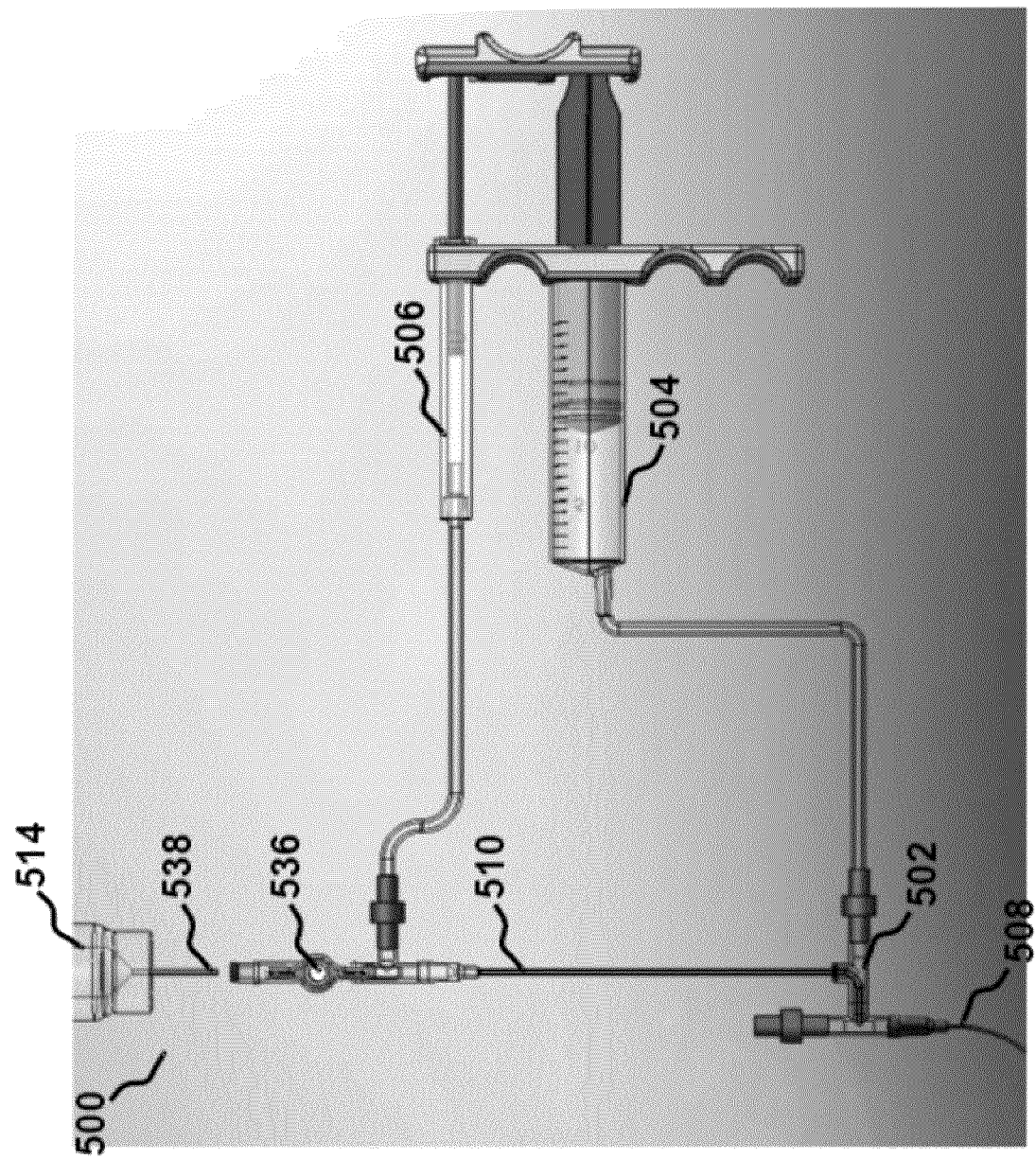
FIG. 7 is a side view of the delivery device of FIG. 5 with a chamber uncoupled from a remainder of the delivery device.

Referring now to FIG. 7, the chamber (514) is shown uncoupled from a remainder of the delivery device (500). The chamber (514) is uncoupled from the fluid control valve (536) for the purpose of filling the chamber (514) with microparticles or carrier fluid, or both. The chamber (514) is uncoupled from the fluid control valve (536) by displacing the chamber (514) in a direction away from the fluid control valve (536), thus disconnecting tubing (538) that extends from the conical portion (526) into the fluid control valve (536). The chamber (514) is coupleable again by reinserting the tubing (538) into the fluid control valve (536).

A side view of the fluid mixer (502) is shown in FIG. 8. The arrow illustrated in FIG. 8 indicates the direction of flow of the transport medium from the source of the transport medium (not shown) to the fluid outlet (not shown). The fluid mixer (502) in this example is a T-junction and includes the conduit (522) and the dispenser (524) disposed within the conduit. In use, the microparticles flow from the dispenser (524), into the transport medium that passes through the fluid mixer (502). The dispenser (524) directs the microparticles in the direction of the flow of the transport medium. The dispenser (524) is substantially concentric with the conduit, for directing the microparticles into the center of the fluid flow.

In use, changing the delivery device 500 may remain the same orientation for both loading and for fluid delivery. Optionally, the orientation of the delivery device 500 may be changed to facilitate removal of gas, such as air, trapped in the chamber (514).

One example of a device that can be loaded with microparticles is the delivery device illustrated in FIG. 5, but without the source of transport medium (504), the source of displacement medium (506), or the chamber (514) that supplies the microparticles to the device.

Figure 9:
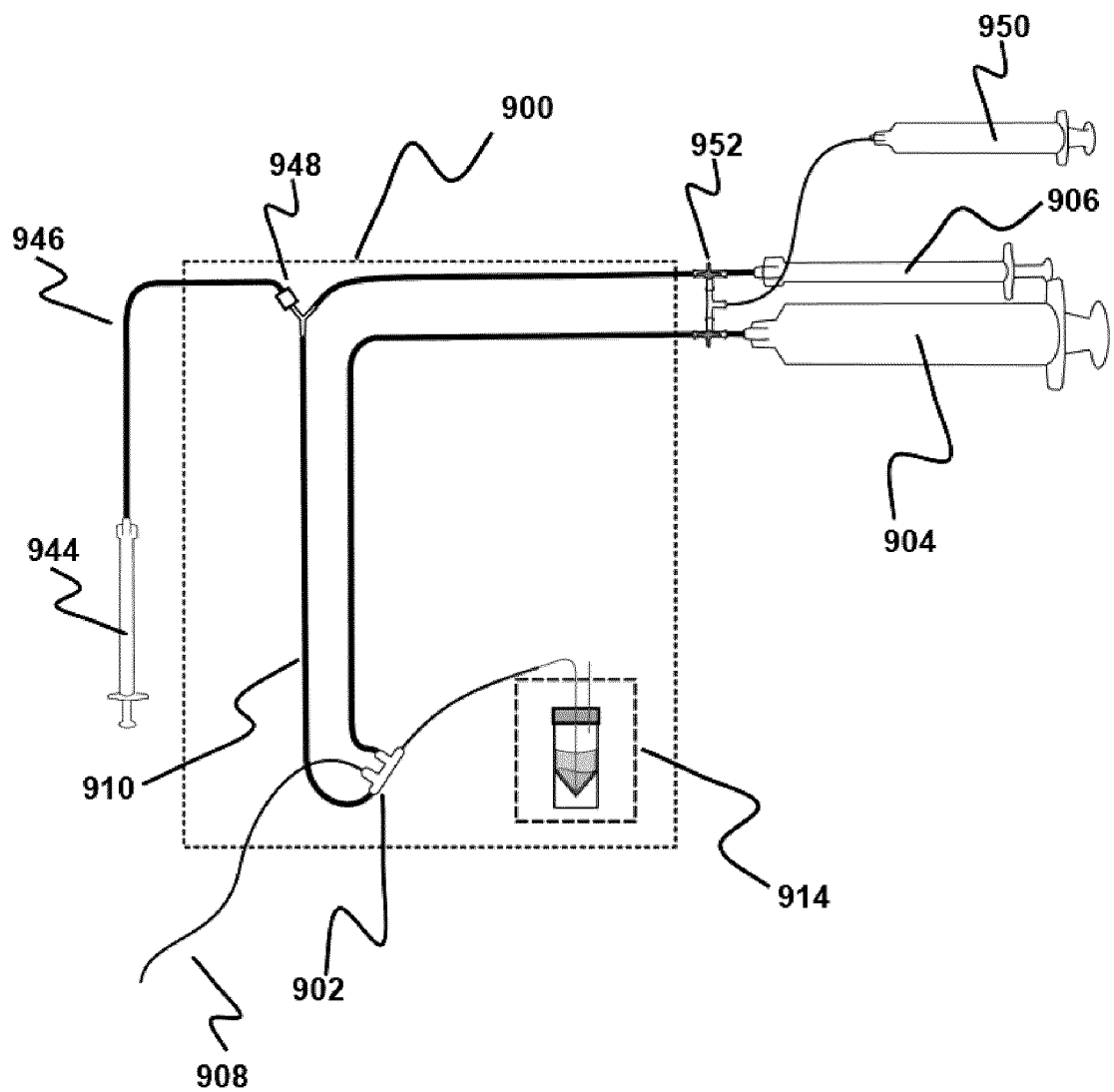
FIG. 9 is a side view of still another example of a delivery device according to the present disclosure.

Reference is now made to FIG. 9, which illustrates another example of a delivery device in accordance with the present disclosure. Many of the features of the delivery device illustrated in FIG. 9 are similar to those shown and described above with reference to FIG. 1 through FIG. 4 and are not described again in detail to avoid obscuring the description. Where similar features are described with reference to FIG. 9, similar reference numerals are utilized, raised by 800.

The delivery device (900) in FIG. 9 is illustrated with a fluid mixer (902) fluidly coupled to a source of transport medium (904), and a source of displacement medium (906), and fluidly coupled to a fluid outlet (908). The delivery device (900) includes the elongate housing (910), which in the present example is tubing. The elongate housing (910) is fluidly coupled to the fluid mixer (902) at a second end, and fluidly coupled to the source of displacement medium (906) at a first end.

In the example illustrated in FIG. 9, the fluid mixer (902) includes a T-junction. The transport medium (904) and the displacement medium (906) enter the T-junction from the two branches and exit the T-junction through the trunk and flow to the fluid outlet (908). As illustrated, the T-junction of the fluid mixer (902) is directly adjacent to a second T-junction. The transport medium (904) enters the fluid mixer (902) after passing through the second T-junction. The T-junction of the fluid mixer (902) and the second T-junction do not need to be directly adjacent to each other, and could instead be separated, for example, by a length of tubing.

In operation, transport medium (904) travels through the fluid mixer (902) and out the fluid outlet (908). The displacement medium (906) travels into the elongate housing (910), and pushes microparticles from the elongate housing (910) into the fluid mixer (902). The transport medium travelling through the fluid mixer (902) carries the microparticles out the fluid outlet (908) for delivery of the transport medium, including the microparticles and the displacement medium, to the patient.

In contrast to the examples described above with respect to FIG. 1, the chamber (914) in the present example is not located fluidly between the elongate housing (910) and the source of the displacement medium (906). The chamber (914) is located outside of the fluid flow path from source of the displacement medium (906) to the liquid outlet (902). In the present example, the chamber (914) is fluidly coupled to the second end of elongate housing (910), through the fluid mixer (902).

The exemplary delivery device illustrated in FIG. 9 additionally includes a source of flushing medium (950), which is fluidly connectable via fluid control valves (952) to fluid outlet (908) via both (i) the elongate housing (910) and (ii) the tubing connecting the transport medium (904) and the fluid outlet (908). The source of flushing medium (950) is optional, as are the fluid control valves (952) that fluidly link the source of displacement medium (906) and the source of transport medium (904).

To load the elongate housing (910) with microparticles from the chamber (914), a loading fluid containing the microparticles is drawn from the chamber (914) into the elongate housing (910) using an aspirating syringe (944) which applies a reduced pressure at the loading fluid outlet (946). A filter (948) is positioned to prevent or inhibit microparticles from being drawn into the aspirating syringe (944) during loading.

Fluid control valves are not illustrated in FIG. 9, though they may be included to direct the flow of fluids into desired portions of the delivery device. For example, the delivery device may include a fluid control valve between the filter (948) and the loading fluid outlet (946). Such a fluid control valve may be closed during delivery of the microparticles to the patient in order to reduce or prevent displacement medium from flowing out the loading fluid outlet (946). In another example, the delivery device may include a fluid control valve between the source of transport medium (904) and the mixer (902). Such a fluid control value may be closed during loading of the elongate housing (910) with microparticles in order to reduce or prevent microparticles from flowing into the tubing connecting the mixer (902) and the source (904) of the transport medium.

One example of a device that can be loaded with microparticles is the delivery device illustrated in FIG. 9, but without the source of transport medium (904), the source of displacement medium (906), the chamber (914) that supplies the microparticles to the device, the aspirating syringe (944), or the source of flushing medium (950).

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A delivery device for intravenous delivery of microparticles to a patient, the delivery device being fluidly connectable to (i) a first source of an injection medium and (ii) a second source of an injection medium, the delivery device comprising:
    a first fluid inlet fluidly connectable to the first source of the injection medium,
    a fluid outlet,
    a fluid mixer fluidly connecting the first fluid inlet to the fluid outlet,
    a second fluid inlet fluidly connectable to the second source of the injection medium,
    a source of microparticles fluidly connecting the second fluid inlet to the fluid mixer; and
    a microparticle trap fluidly located between the source of microparticles and the fluid mixer, wherein the microparticle trap comprises a bend in tubing connecting the source of microparticles to the fluid mixer, wherein the bend is at least about 90 degrees and the bend stops the microparticles from entering the fluid mixer when the device is in a loading orientation and the microparticles are not being fluidly driven into the fluid mixer;
    wherein, when fluid flows from the second source of the injection medium into the delivery device:
        the second injection medium fluidly drives microparticles from the source of microparticles into the fluid mixer, and
        the fluid outlet dispenses to the patient an injection medium that comprises the microparticles.

2. The delivery device according to claim 1, wherein the source of microparticles comprises an elongate housing holding the microparticles, wherein the elongate housing is fluidly connected at one end to the fluid mixer and fluidly connectable at a distal end to the second source of the injection medium.

3. The delivery device according to claim 2, wherein delivery device defines a chamber fluidly located between the elongate housing and the second fluid inlet.

4. The delivery device according to claim 3, wherein the chamber comprises a conical portion that funnels the microparticles located in the chamber into the elongate housing when the delivery device is in a microparticle-loading orientation.

5. The delivery device according to claim 1, wherein the fluid mixer comprises:
    a conduit for the first injection medium, the conduit fluidly connecting the first fluid inlet with the fluid outlet; and
    a dispenser disposed within the conduit, the dispenser fashioned to add microparticles to the injection medium in the direction of the flow of the injection medium passing through the fluid mixer.

6. The delivery device according to claim 5, wherein the conduit and the dispenser are concentric tubes, with the dispenser disposed within the conduit.

7. The delivery device according to claim 1, wherein the fluid mixer is configured to flow the first injection medium in a substantially horizontal orientation when the delivery device is in a delivery orientation.

8. The delivery device according to claim 1, wherein the fluid mixer is configured to flow the first injection medium in a substantially vertical orientation when the delivery device is in a delivery orientation.

9. The delivery device according to claim 1, wherein the microparticle trap comprises an approximately 90 degree bend or a U-turn in the tubing connecting the source of microparticles to the fluid mixer.

10. The delivery device according to claim 1, wherein the source of the first injection medium is different from the source of the second injection medium, optionally wherein the first and the second injection mediums are the same.

11. The delivery device according to claim 1, wherein the delivery device defines a flow path for the microparticles, the microparticle flow path comprising the source of microparticles, the fluid mixer, and the fluid outlet, and all fluid connections therebetween.

12. The delivery device according to claim 11, wherein the diameter of the microparticle flow path is at least three times the average diameter of the microparticles.

13. The delivery device according to claim 11, wherein the cross section of the microparticle flow path is substantially constant from the source of microparticles to the fluid mixer.

14. The delivery device according to claim 1, wherein the microparticles are loaded in the source of microparticles at a packing efficiency from about 80% to about 40%.

15. The delivery device according to claim 1, wherein the microparticles have a specific gravity that is greater than a specific gravity of the injection medium.

16. The delivery device according to claim 2, wherein the elongate housing is above the microparticle trap when the delivery device is in the loading orientation, and the loading orientation and the microparticle trap together allow the microparticles to settle in the elongate housing without entering the fluid mixer when the microparticles are not being fluidly driven into the fluid mixer.

17. A delivery device for intravenous delivery of microparticles to a patient, the delivery device being fluidly coupleable to a transport medium and a displacement medium, the delivery device comprising:

a first fluid inlet fluidly coupleable to the transport medium, a fluid outlet, a fluid mixer fluidly coupling the first fluid inlet to the fluid outlet, a source of microparticles fluidly coupled to the fluid mixer, a microparticle trap fluidly located between the source of microparticles and the fluid mixer, wherein the microparticle trap comprises a bend in tubing connecting the source of microparticles to the fluid mixer, wherein the bend is at least about 90 degrees and the bend stops the microparticles from entering the fluid mixer when the device is in a loading orientation and the microparticles are not being fluidly driven into the fluid mixer; and a second fluid inlet fluidly coupleable to the displacement medium, the second fluid inlet in fluid communication with the fluid mixer, for driving, utilizing the displacement medium, the microparticles into the fluid mixer and out the fluid outlet via the transport medium.

18. The delivery device according to claim 17, wherein the source of microparticles comprises an elongate housing holding the microparticles, and wherein the elongate housing is above the microparticle trap when the delivery device is in the loading orientation, and the loading orientation and the microparticle trap together allow the microparticles to settle in the elongate housing without entering the fluid mixer when the microparticles are not being fluidly driven into the fluid mixer.

19. A device for loading with microparticles for intravenous delivery to a patient, the device being fluidly coupleable to a transport medium and a displacement medium, the device comprising:

a first fluid inlet fluidly coupleable to the transport medium, a fluid outlet, a fluid mixer fluidly coupling the first fluid inlet to the fluid outlet, a receptacle configured to hold microparticles, the receptacle fluidly coupled to the fluid mixer, a microparticle trap fluidly located between the receptacle and the fluid mixer, wherein the microparticle trap comprises a bend in tubing connecting the source of microparticles to the fluid mixer, wherein the bend is at least about 90 degrees and the bend stops the microparticles from entering the fluid mixer when the device is in a loading orientation and the microparticles are not being fluidly driven into the fluid mixer; and a second fluid inlet fluidly coupleable to the displacement medium and fluidly coupled to the receptacle, the receptacle fluidly coupling the second fluid inlet to the fluid mixer.

20. The device according to claim 19, wherein the receptacle is fluidly connected to the second fluid inlet at a first end, and is fluidly connected to the fluid mixer at a second end.

21. The device according to claim 19, further comprising a loading fluid inlet fluidly connected to the receptacle.

22. The device according to claim 21, wherein the receptacle: (a) fluidly couples the loading fluid inlet and the fluid mixer, or (b) fluidly couples the loading fluid inlet and a loading fluid outlet.

23. The device according to claim 22, further comprising a filter fluidly located between the receptacle and the loading fluid outlet.

24. The device according to claim 19, wherein the fluid mixer is a T-junction.

25. The delivery device according to claim 19, wherein the receptacle configured to hold microparticles is above the microparticle trap when the delivery device is in the loading orientation, and the microparticles settle in the receptacle without entering the fluid mixer when the microparticles are loaded by gravity into the receptacle.

* * * * *